(12) United States Patent
Kral et al.

(10) Patent No.: US 6,555,054 B1
(45) Date of Patent: Apr. 29, 2003

(54) FLOW THROUGH RACK FOR CONTACT POINT STERILIZATION OF RACK SUPPORTED MEDICAL DEVICES

(75) Inventors: Jude A. Kral, Twinsburg, OH (US); Richard A. Schieman, Novelty, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/232,068

(22) Filed: Jan. 15, 1999

(51) Int. Cl.⁷ ............... A01N 2/08; B65D 83/10; A47F 1/04; B08B 3/00
(52) U.S. Cl. ............... 422/28; 422/297; 422/300; 206/363; 206/438; 211/60.1; 211/66; 134/198
(58) Field of Search ............... 422/28, 31, 33, 422/29, 292, 297, 300; 206/363, 438; 211/60.1, 66; 134/198–199

(56) References Cited

U.S. PATENT DOCUMENTS

| | | | | |
|---|---|---|---|---|
| 4,281,674 A | * | 8/1981 | Tanaka et al. | 134/95 |
| 4,288,882 A | * | 9/1981 | Takeuchi | 15/88 |
| 4,552,728 A | * | 11/1985 | Taylor | 422/300 |
| 4,748,007 A | * | 5/1988 | Gaudion et al. | 422/300 |
| 5,090,433 A | * | 2/1992 | Kamaga | 134/169 C |
| 5,225,160 A | * | 7/1993 | Sanford et al. | 422/28 |
| 5,552,115 A | * | 9/1996 | Malchesky | |
| 5,759,490 A | | 6/1998 | Malchesky | 422/28 |
| 5,833,935 A | * | 11/1998 | Malchesky | 422/300 |
| 5,993,754 A | * | 11/1999 | Lemmen et al. | 422/293 |
| 6,073,781 A | * | 6/2000 | Puglisi | 211/70.6 |
| 6,190,609 B1 | * | 2/2001 | Chapman et al. | 422/24 |

OTHER PUBLICATIONS

Porex® Porous Plastics High Performance Materials.

* cited by examiner

*Primary Examiner*—Elizabeth McKane
*Assistant Examiner*—Monzer R Chorbaji
(74) *Attorney, Agent, or Firm*—Fay, Sharpe, Fagan, Minnich & McKee, LLP

(57) ABSTRACT

A flow-through rack assembly (14) includes porous hangers (44) which support items to be decontaminated within a decontamination chamber (12). A plurality of nozzles (16) spray a decontaminant fluid, such as peracetic acid, over the items. The rack assembly includes tubes (42) which convey a portion of the decontaminant fluid under pressure to internal channels (52) of the porous hangers. The fluid permeates the hanger surface, flowing over regions of the items which are in contact with the hangers. The rack assembly ensures decontamination of those regions which may be otherwise inaccessible to fluid sprayed from the nozzles.

26 Claims, 4 Drawing Sheets

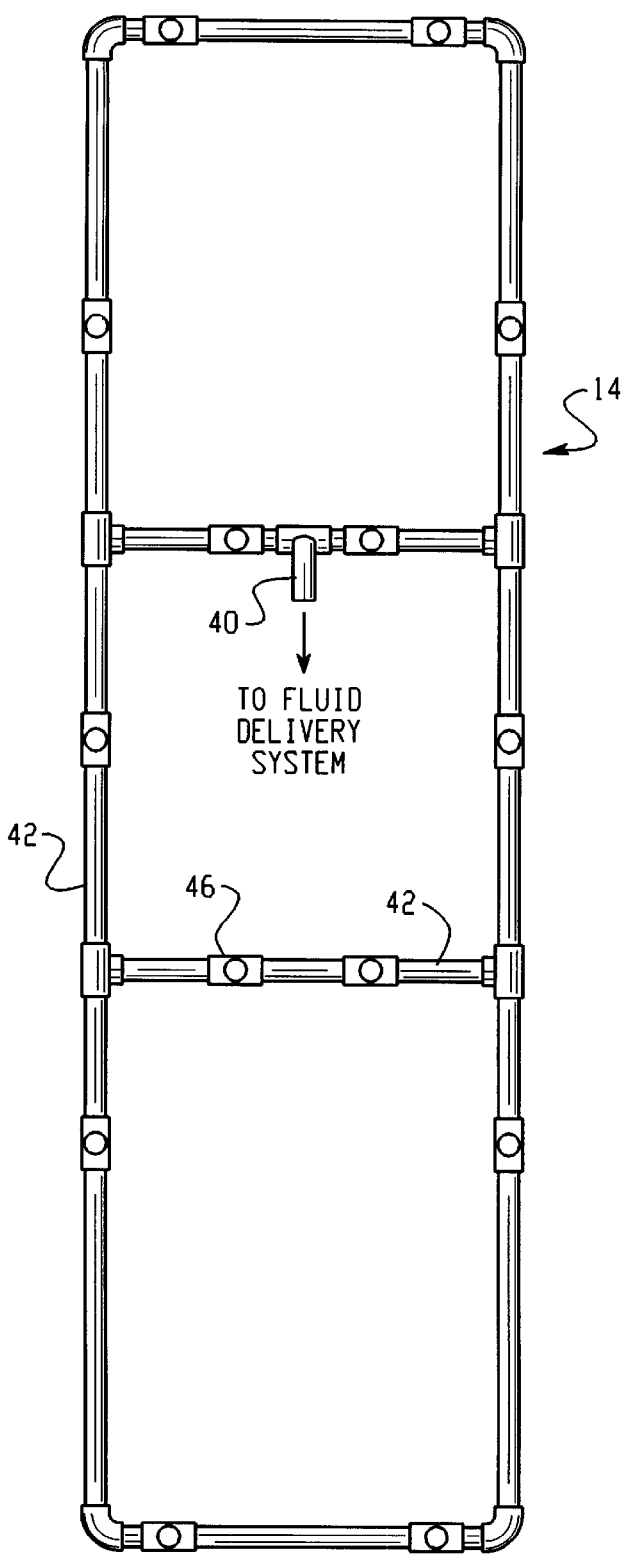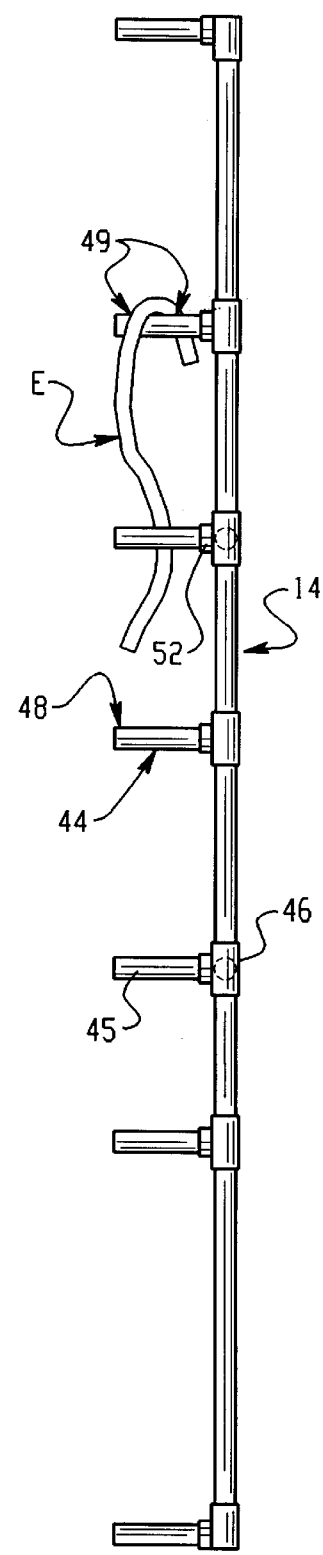
Fig. 2
Fig. 3

FLOW THROUGH RACK FOR CONTACT POINT STERILIZATION OF RACK SUPPORTED MEDICAL DEVICES

BACKGROUND OF THE INVENTION

The present invention relates to the decontamination arts. It finds particular application in conjunction with the cleaning and microbial decontamination of medical instruments and equipment and will be described with particular reference thereto. It should be appreciated, however, that the invention is also applicable to other systems in which entire outer surfaces of rack-supported items are to be contacted with a liquid.

The reuse of a wide variety of medical and dental equipment, such as endoscopes, has lead to the development of cleaning and microbial decontamination systems for ensuring decontamination of the equipment. The equipment is often unable to withstand the high temperatures or pressures of steam sterilization because of the materials used in construction. As a consequence, liquid microbial decontamination systems have recently been utilized for sterilization or disinfection of such equipment.

Commonly, a technician rinses the used equipment, then mixes a liquid disinfectant or sterilant composition and manually immerses the equipment to be microbially decontaminated in the composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like. If the equipment is disinfected without cleaning, biological materials may remain on the equipment. The biological material can break down to pyrogens or other toxic substances.

Recently, systems have been developed which automate the decontamination process. U.S. Pat. Nos. 4,731,222; 5,217,698; and 5,552,115 disclose examples of such automated liquid systems. A reproducible amount of a decontaminant is delivered to the microbial decontamination system from a single dose package. U.S. Pat. Nos. 5,037,623 and 5,662,866, for example, disclose cups which contain a measured dose of either a liquid peracetic acid concentrate or powdered reagents.

To release the sterilant or disinfectant into the fluid flow path of a microbial decontamination system, the cup is inserted into a well in fluid communication with the system. The cup is opened and water is circulated through the well. The decontaminant solution formed is transported to a sterilization chamber where it is brought into contact with items to be decontaminated.

For effective decontamination, all of the surfaces of the items should be contacted with the decontaminant solution. However, to arrange the equipment in the decontamination chamber, various support members, such as clips, are generally used. These tend to impede the passage of the liquid decontaminant to adjacent regions of the equipment surfaces. To address this problem, U.S. Pat. No. 5,759,490 discloses a porous clip for shaping and positioning catheters in a countertop sterilizer. The clip is fabricated from an open-celled porous material which permits the passage of the decontaminant to the portion of the catheter gripped by the clip.

For larger items, such as endoscopes, however, it is convenient to support these on racks and spray the disinfectant over the outer surfaces, while simultaneously delivering liquid disinfectant or sterilant to the internal passageways of these items. Contact areas between the endoscopes and the racks lead to reduced access of the decontaminant. This tends to result in incomplete decontamination of the equipment.

The present invention provides for a new and improved porous rack assembly which overcomes the above-referenced problems and others.

SUMMARY OF THE INVENTION

In accordance with one aspect of the present invention, a flow-through rack assembly for supporting an item to be decontaminated is provided. The assembly includes at least one porous hanger for supporting the item, the hanger being formed of a porous material which permits a decontaminant fluid to permeate therethrough and contact the item, and a fluid flow line which supplies the decontaminant fluid under pressure to the hanger.

In accordance with another aspect of the present invention, a method of decontamination is provided. The method includes supporting an item to be sterilized on a porous hanger and spraying surfaces of the item with a decontaminant fluid. The method further includes passing a portion of the decontaminant fluid under pressure through the porous hanger to contact a portion of the surfaces of the item which is in contact with the hanger.

In accordance with another aspect of the present invention, a decontamination system is provided. The system includes a chamber for receiving items to be decontaminated and a flow-through rack assembly supported within the chamber for supporting at least one of the items to be decontaminated. The rack assembly includes at least one porous hanger for supporting the item. The hanger is formed from a porous material which permits a decontaminant fluid permeate therethrough and contact at least one item. The assembly also includes a fluid flow line which supplies the decontaminant fluid to an interior of the porous hanger.

One advantage of the present invention is that exterior surfaces of equipment are thoroughly decontaminated.

Another advantage of the present invention is that complete decontamination of several large pieces of equipment is achieved in a relatively short time.

Yet other advantages of the present invention derive from the spraying of a decontamination fluid over large items, reducing the volume of decontaminant used, as compared with immersion systems.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is an enlarged schematic front view of the rack assembly of FIG. 1;

FIG. 3 is an enlarged schematic side view of the rack assembly of FIG. 1;

DETAILED DESCRIPTION OF THE PREFERRED EMBODIMENTS

Figure 1:
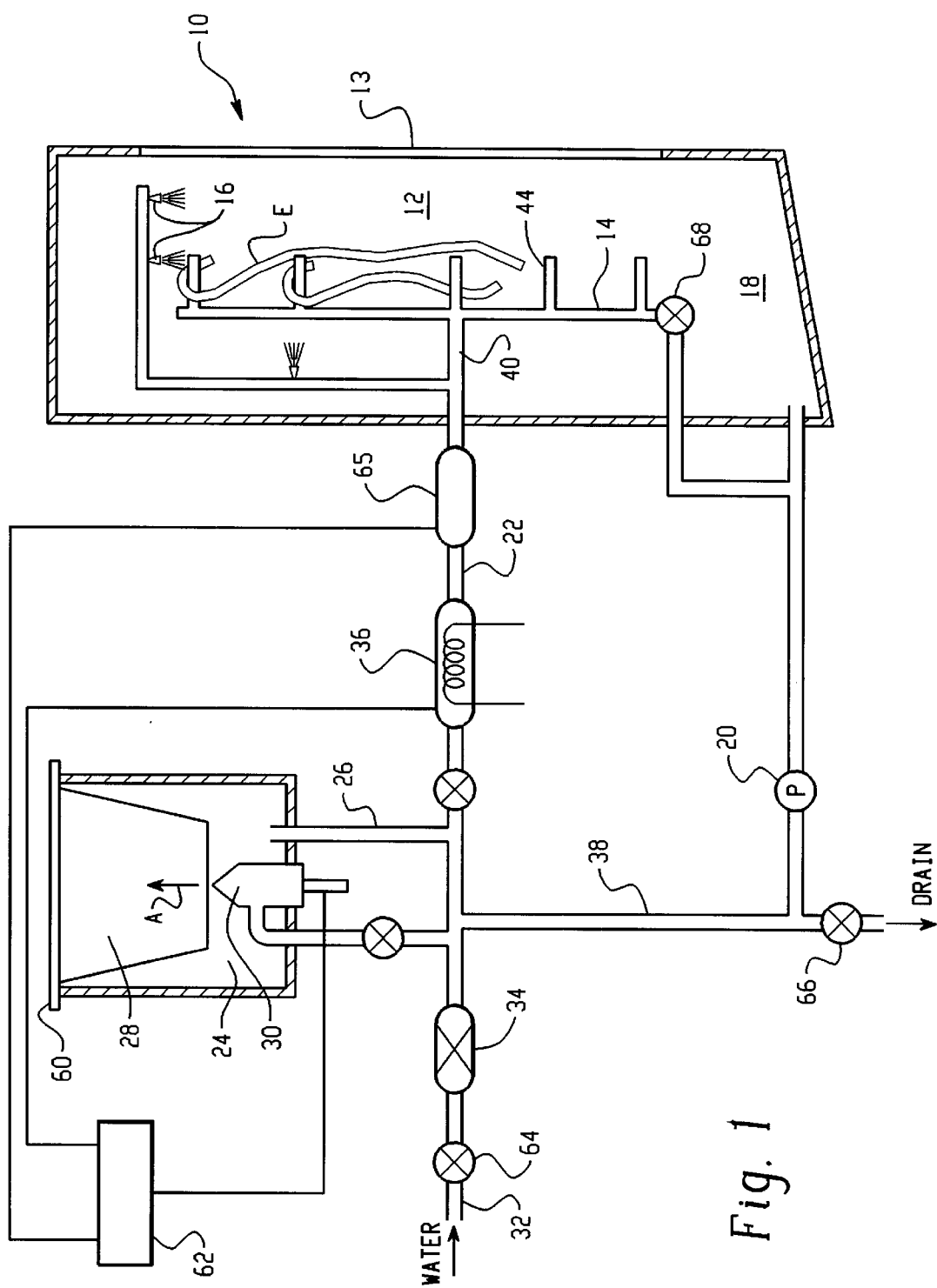
FIG. 1 is a plumbing diagram of a decontamination unit and rack assembly according to the present invention.

With reference to FIG. 1, an automated liquid decontamination system for microbially decontamination of medical and pharmaceutical instruments, and the like is shown. For ease of reference, the words decontamination, decontaminant, and the like, are used to denote all forms of microbial decontamination, including sterilization and disinfection. The system includes a decontamination cabinet 10 which defines a chamber 12. Items to be decontaminated are loaded into the chamber through a door 13 in a wall of the decontamination cabinet. Large items, such as endoscopes, are hung within the chamber on a flow-through rack assembly 14. Nozzles 16, within the chamber, spray a decontaminant fluid, such as a disinfectant or sterilant solution over the items.

A collection tank or sump 18 at the base of the cabinet 10 receives the sprayed decontaminant fluid as it drips off the items. A pump 20 delivers the decontaminant fluid under pressure to the nozzles 16 and the rack assembly 14 through a fluid inlet line 22. A well 24 for receiving a concentrated decontaminant is in fluid communication with the fluid inlet line via a decontaminant line 26.

A disposable container or cup 28, which holds a measured dose of the concentrated decontaminant, is positioned in the well. A cutter assembly 30 opens the cup to release the decontaminant by moving upwardly into the well in the direction of arrow A.

A water inlet line 32 delivers fresh water to the well to dilute the decontaminant concentrate to form a decontaminant fluid at a selected working concentration of the decontaminant. The water used may be tap water or treated water, such as distilled water. The quantity of water entering the decontamination system is regulated to provide a decontaminant fluid of a desired nominal concentration of the decontaminant flowing through the chamber. The water is first passed through a microporous filter 34 which filters out particles of dirt and microorganisms.

A heater 36 disposed in the fluid inlet line 22. heats the decontaminant fluid to a desired temperature for effective decontamination. A return fluid line 38 returns the sprayed decontaminant fluid from the sump 18 to the nozzles 16 and the rack assembly 14. At least a portion of the sprayed fluid is directed through the well to ensure thorough mixing of the concentrated decontaminant in the fluid and dissolution of any solid components.

Figure 4:
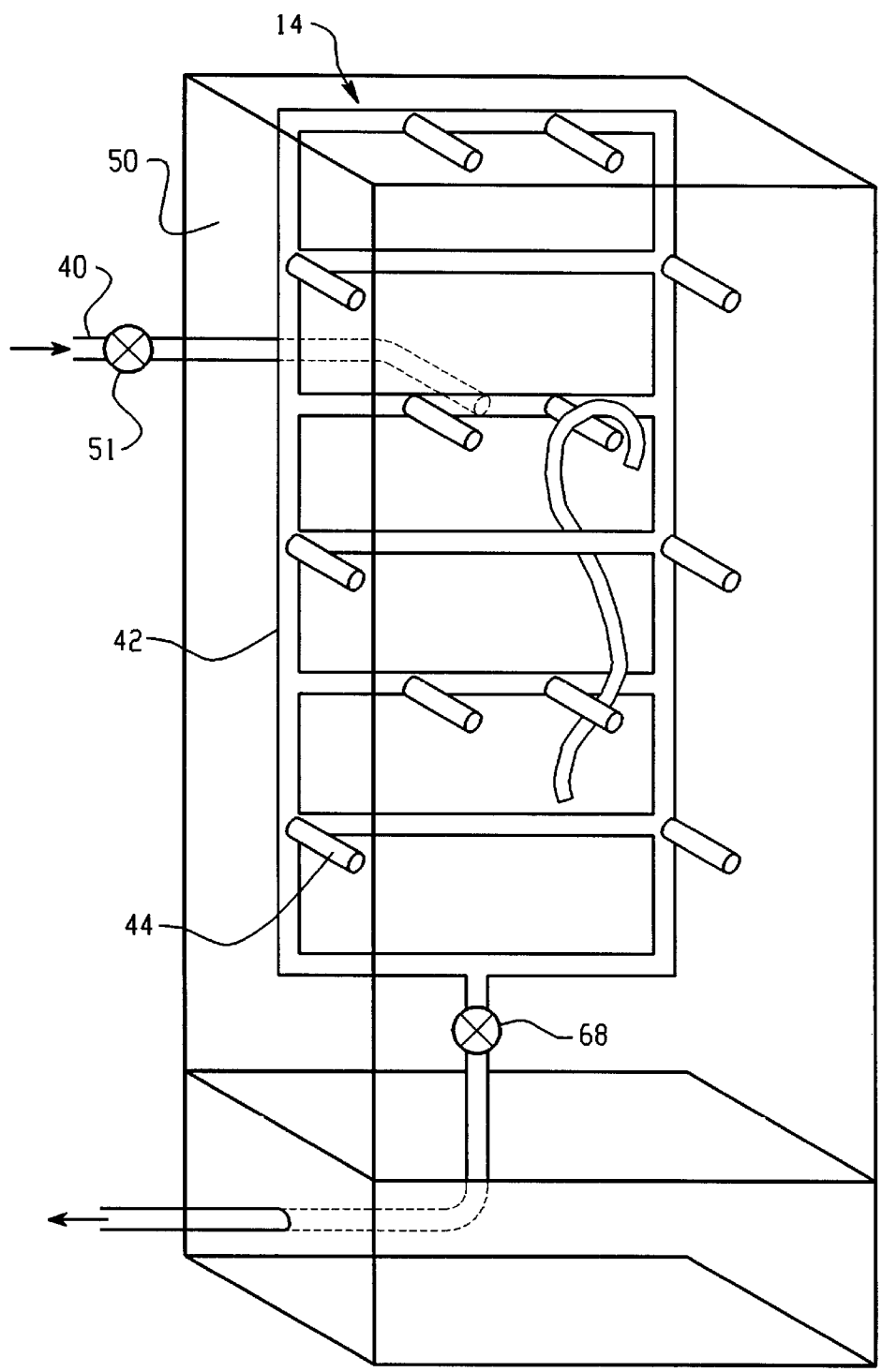
FIG. 4 is an enlarged perspective view of the decontamination chamber and rack assembly of FIG. 1.

With reference also to FIGS. 2, 3, and 4, the rack assembly 14 is connected to the fluid inlet line 22 by a rack inlet line 40. The rack assembly includes a number of interconnected tubes or passageways 42. The decontaminant fluid passes through the tubes 42 to porous hangers 44, such as posts or sleeves, which extend generally perpendicularly at intervals from the tubes 42. The posts have at least an outer portion which is formed from a porous material 45. Connection members 46 are connected between the tubes 42 and the hangers 44 to provide leak tight connections. The decontaminant fluid flows through the porous hangers and permeates through the porous material 45 to external surfaces 48 of the hangers.

The migration of the decontaminant fluid through the porous material 45 ensures the entire outer surface 48 of the hanger is wetted with the decontaminant fluid, and not only those areas accessible to the spray from the nozzles 16. Because the decontaminant fluid is under pressure, provided by the pump 20, the outer surface of the hanger is continuously supplied with fresh decontaminant solution. Endoscopes E, and the like, which are supported on the hangers, are thus contacted by the decontaminant fluid at areas of contact 49 of the instruments with the external surfaces 48 of the hangers 44. In addition, some of the decontaminant fluid sprayed from the nozzles 16 falls on the surfaces 48 of the hangers, wetting the porous material 45 from the outside. This fluid is also able to migrate through the porous material to the areas of contact 49 between the endoscope and the hanger.

The tubes 42 are preferably constructed of a fairly rigid material, such as plastic, which is resistant to the chemicals used in the decontamination system. In addition, the tubes are sufficiently strong to support the weight of the hangers 44 and the items to be decontaminated which are supported thereon.

The rack assembly 14 may be disposed wholly or partially within the chamber 12. With particular reference to FIG. 4, the tubes 42 may be supported on an interior surface of a rear wall 50 of the cabinet 10. Alternatively, the tubes may be located outside the cabinet 10, with the connection members 46 extending into the chamber 12 through openings (not shown) in the rear wall 50.

The pressure of the decontaminant fluid supplied to the rack may be adjusted to maintain a steady flow of the decontaminant fluid to the surface 48 of the porous material, for example by adjusting the pump 20 or by adjusting a variably adjustable valve 51 in the rack inlet line 40.

The porous material 45 is preferably a rigid material which provides numerous internal passageways for slow migration of the decontaminant through the material. Suitable porous materials include expanded polyethylene, expanded Teflon, expanded nylon 6, porous ceramics, porous sintered metals, and the like. Other suitable polymers include nylon, polysulfone, polycarbonate, polyphthalate carbonate, polytetrafluoroethylene, polyvinylidene fluoride, polyetherimide, styrene-butadiene copolymers, polyphenylene oxide, polypropylene, and the like. Where the decontaminant includes a strong oxidant or acid, the porous material is preferably one which has a strong oxidation or acid resistance, such as such as an expanded plastic material, sintered titanium, or sintered stainless steel. One particularly preferred porous material is an open-celled plastic material, such as POREX™.

The porous material has a pore size sufficient to permit the flow of the decontaminant therethrough during the period of decontamination. Normally available micron pore sizes of 3 to 25 microns, and above, have been found to provide for sufficient flow of the decontaminant. Of course, larger pore sizes will provide a greater decontaminant fluid flow. Longitudinally extending passages, spiral passages, bores, and the like may be provided through the porous material to promote yet greater fluid flow.

Preferably, the porous material has sufficient strength to support the weight of the wet medical device. Alternatively, an internal support is provided.

Figure 5:
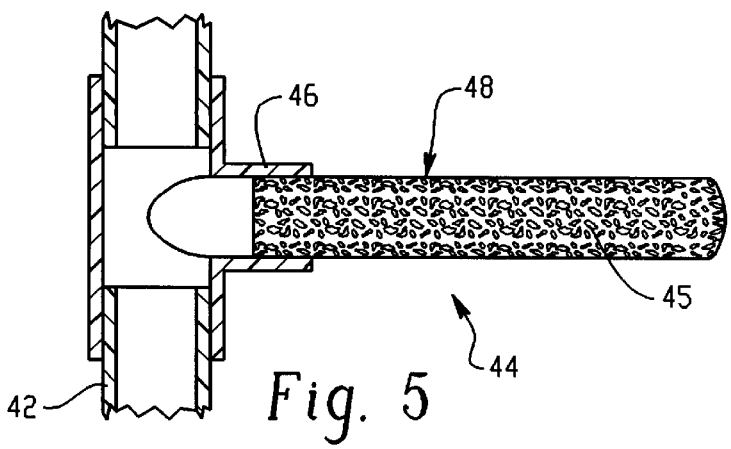
FIG. 5 is an enlarged schematic side view of one embodiment of the porous hanger of the rack assembly of FIG. 1.
Figure 6:
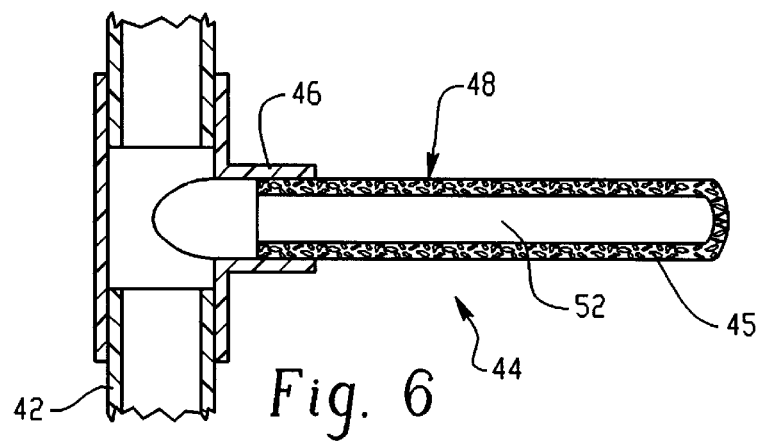
FIG. 6 is an enlarged schematic side view of another preferred embodiment of the porous hanger of the rack assembly of FIG. 1.

In one embodiment, the hanger is formed entirely from the porous material, as shown in FIG. 5. In another embodiment, the hanger is hollow with an internal channel or bore 52 passing axially along the center of the hanger. The channel carries the decontaminant from the tube 42 to the interior of the hanger, as shown in FIG. 6.

Figure 7:
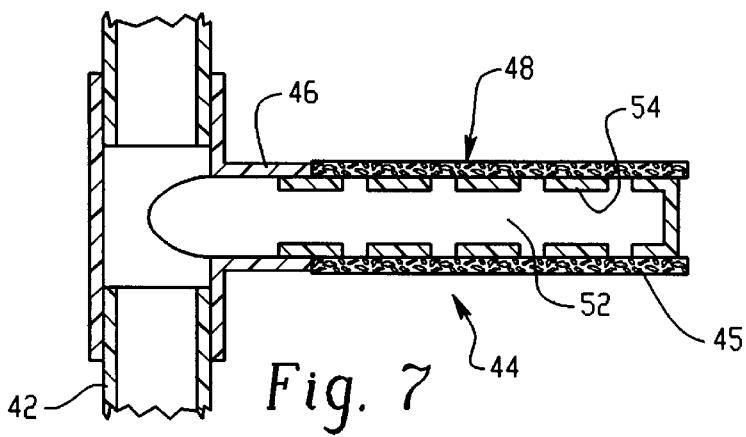
FIG. 7 is an enlarged side view of yet another preferred embodiment of the porous hanger of the rack assembly of FIG. 1 and, FIG. 8 is an enlarged cut-away side view of a still further embodiment of the porous hanger of FIG. 1.

In another embodiment, a rigid cylindrical internal support tube 54, positioned between the channel 52 and the porous material 45 is provided to support the weight of the porous material, as shown in FIG. 7. In this embodiment, the support tube is perforated to allow the passage of the decontaminant fluid therethrough. The support tube may be connected with the connection member 46, or formed integrally therewith. The porous material 45 may take the form of a sponge jacket or sleeve which is held in place on the support tube by friction. This allows the porous material to be replaced, as necessary, without removing the connection member.

Figure 8:
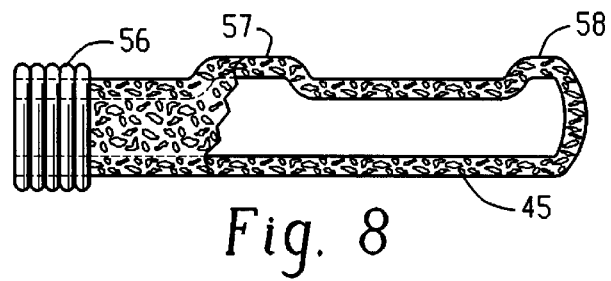

With reference to FIG. 8, the hanger is optionally attached to the connection member by a connector 56, such as a screw fitting or a quick connect coupling. The porous material may define a hook shape for holding the endoscopes E more securely. For example, the porous material 45 may define inner and outer protrusions. 57 and 58, respectively, on an upper surface of the porous material for receiving an endoscope therebetween.

In a typical decontamination cycle, items to be decontaminated are first inserted into the cabinet 10 through door 13. Large items are hung over the porous hangers 44 of the rack assembly. A fresh decontaminant cup 28 is inserted into the well 24 and a lid 60 closed and latched over the well. A controller 62 preferably controls the operation of the components of the system, including valves, cup cutter 30, heater 36, pump 20, and the like. The controller signals a valve 64 in the water inlet line 30 to open, allowing water to circulate through the fluid lines 22, 26, and 38. Once the desired quantity of water has been admitted to the system, the valve 64 is closed.

The controller 62 then signals the cutter assembly 30 to open the cup. Water is forced into the cup, flushing the concentrated decontaminant out of the cup. The decontaminant fluid formed then enters the fluid lines 22, 26 and is sprayed over the items to be decontaminated. A sensor 65, in fluid communication with the fluid flow lines 22 and 38, optionally detects the concentration of the decontaminant in the circulating fluid to make sure a threshold level for adequate decontamination is present. The pump 20 pumps the sprayed fluid from the sump 18 into the well 24 and through the fluid inlet line 22. The controller 62 signals the heater 36 to heat the decontaminant fluid to the desired temperature. The decontaminant fluid is sprayed through the nozzles 16 over the items to be cleaned and is also directed through the rack assembly 14. At the end of the decontamination part of the cycle, the controller signals a drain valve 66 in the return fluid line 38 to open and the decontaminant fluid is pumped out of the system and to a drain.

An additional valve, such as a check valve 68, for the rack assembly 14, opens to drain decontaminant fluid from the tubes 42. Preferably, the check valve 68 is biased to a normally open state and closes automatically under the biasing force of the above-atmospheric pressure of fluid being pumped through the tubes. When the excess pressure is removed, the valve returns to the open position, allowing fluid remaining in the tubes to drain out by gravity. This fluid passes with the rest of the fluid being drained to the drain through drain valve 66.

Optionally, the valve 64 in the water inlet line is opened again to allow additional fresh water into the system to flush the decontaminant fluid from the fluid lines 22 and the well 24 and to rinse the decontaminated items. The fresh water may also be directed to the rack assembly 14.

Various antimicrobial agents may be utilized for the decontaminant. In one preferred embodiment, the decontaminant is a concentrated solution of peracetic acid. It is also contemplated using powdered reagents which react in a common solvent to generate peracetic acid, chlorine gas, hydrogen peroxide, hypochlorous acid, hypochlorite, or other strong oxidants which have biocidal effects.

Other substances may also be circulated through the nozzles 16 and the rack assembly 14, such as cleaning fluids, buffers for modifying the pH of the decontaminant solution, surfactants for improved penetration of the decontaminant into cracks and crevices, and corrosion inhibitors for protecting the system and equipment to be decontaminated from the corrosive effects of the decontaminant. Such substances may be included as measured doses in the cup or introduced to the decontaminant fluid separately.

Preferred copper and brass corrosion inhibitors include azoles, benzoates, other five-membered ring compounds, benzotriazoles, tolytriazoles, mercapto-benzothiazole, and the like. Other anti-corrosive buffering compounds include phosphates, molybdates, chromates, dichromates, tungstates, vanadates, other borates, and combinations thereof. These compounds are effective for inhibiting steel and aluminum corrosion. For hard water in which calcium and magnesium salts may tend to precipitate, a sequestering reagent, such as sodium hexametaphosphate is also included.

The corrosion inhibitory agents are selected in accordance with the nature of the materials in the items being decontaminated with the decontaminant fluid. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and orthophenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Suitable copper and brass corrosion inhibitors include triazoles, azoles, benzoates, tolyltriazoles, dimercaptothiadiazoles, and other five-membered ring compounds. Particularly preferred copper and brass corrosion inhibitors include sodium salts of benzotriazole and tolyltriazole which are preferred due to their stability in the presence of strong oxidizing compounds. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and also leave deposits on parts of the system. In such cases, a sequestering agent appropriate to prevent precipitation, such as sodium hexametaphosphate (HMP), or trisodium nitrolotriacetic acid (NTA $Na_3$), is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated.

Surfactants are particularly important in decontaminating complex medical instruments which may contain microbial contaminants in crevices, joints, and lumens. Surfactants usable in accordance with the present invention include anionic, cationic, nonionic, amphoteric, and/or zwitterionic surfactants. Examples of nonionic surfactants usable in the present invention include fatty alcohol polyglycol ethers, nonylphenoxypoly (ethyleneoxy) ethanol, and ethoxylated polyoxypropylene.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A flow-through rack assembly for supporting an item to be decontaminated, the assembly comprising:
    at least one hanger for supporting the item by an exterior surface of the item, the hanger being fluid permeable to permit a decontaminant fluid to permeate therethrough and contact the exterior surface of the item hanging thereon; and,
    a fluid flow line which supplies the decontaminant fluid under pressure to the hanger, the hanger including:
        a fluid permeable hanger element which defines an interior passage with an open end in fluid communication with the fluid flow line and a closed end, the hanger defining an exterior, item supporting surface on which the item is hung, such that when item is hung on the item supporting surface, the decontaminant fluid flows through the fluid permeable hanger element to the exterior item supporting surface and wets the item exterior surface with the decontaminant fluid.

2. The rack assembly of claim 1, wherein the fluid permeable hanger element includes a plurality of hanger elements for supporting and positioning a plurality of items.

3. The rack assembly of claim 1, further including a decontaminant fluid inlet for delivering decontaminant fluid to the fluid flow line.

4. The rack assembly of claim 1, wherein the fluid permeable hanger element includes a porous material which is an open celled plastic material.

5. The rack assembly of claim 1, wherein the fluid permeable hanger element includes a porous material which is sintered.

6. The rack assembly of claim 1, wherein the hanger element is an elongated cylinder and defines an internal bore.

7. The rack assembly of claim 1, further including:
    at least one connection member which releasably connects the at least one hanger element to the fluid flow line.

8. The rack assembly of claim 1, wherein the hanger element is formed entirely from a porous material.

9. The rack assembly of claim 1, further including:
    a drain outlet for draining the decontaminant fluid from the fluid flow line.

10. The rack assembly of claim 9, wherein a normally-open check valve closes the drain outlet when decontaminant fluid in the tubes is at a pressure which is above atmospheric.

11. A flow-through rack assembly for supporting an item to be decontaminated, the assembly including:
    at least one porous hanger for supporting the item, the hanger permitting a decontaminant fluid to permeate therethrough and contact the item, the hanger including:
        a perforated tubular member which defines an internal bore, and,
        a sleeve of a porous open-celled or sintered material covering the tubular member; and,
    a fluid flow line which supplies the decontaminant fluid under pressure to the hanger internal bore.

12. A method of decontamination comprising:
    supporting an item to be sterilized on at least one porous hanger with a surface portion of an exterior wall of the item being in contact with the porous hanger;
    spraying surfaces of the item with a decontaminant fluid, the sprayed fluid dripping off the surfaces into a collection tank; and
    passing a portion of the decontaminant fluid under pressure through the porous hanger to contact the surface portion of the item which is in contact with the hanger.

13. The method of claim 12, further including draining the decontaminant from the hanger.

14. The method of claim 12, wherein the porous hanger defines an interior passage with a closed end.

15. A decontamination system including:
    a chamber for receiving items to be decontaminated;
    a flow-through rack assembly supported within the chamber for supporting at least one of the items to be decontaminated, the rack assembly including:
        at least one hanger for supporting the item, the hanger defining a closed interior passage and being formed from a material which permits a decontaminant fluid permeate from the interior passage therethrough; and
        a fluid flow line which supplies the decontaminant fluid to the closed interior passage of the hanger under pressure such that the pressure urges the decontaminant fluid to permeate through the fluid permeable material and wet surfaces of the supported item in contact with the hanger.

16. A decontamination system comprising:
    a chamber for receiving items to be decontaminated;
    spray nozzles disposed within the chamber for spraying cleaning fluid over the items to be decontaminated;
    a flow-through rack assembly supported within the chamber for supporting at least one of the items to be decontaminated, the rack assembly including:
        at least one porous hanger for supporting the at least one item, the hanger comprising a perforated rigid cylindrical tube with a closed end which permits a decontaminant fluid permeate therethrough and contact the at least one item; and
        a fluid flow line fluidly connected with the porous hanger which supplies the decontaminant fluid to an interior of the porous hanger, such that the decontaminant fluid flows through the cylindrical tube to wet a surface of the at least one item in contact with the hanger.

17. A decontamination system comprising:

a chamber for receiving items to be decontaminated;

a flow-through rack assembly supported within the chamber for supporting at least one of the items to be decontaminated, the rack assembly including:
- at least one porous hanger for supporting the item, the hanger permitting a decontaminant fluid to permeate therethrough and contact the at least one item, the porous hanger including:
  - a rigid tube with a perforated portion and a closed end, and,
  - a porous sleeve on which the at least one item is supported covering at least the perforated portion of the rigid tube; and
- a fluid flow line which supplies the decontaminant fluid to an interior of the porous hanger.

18. A decontamination system comprising:

a chamber for receiving items to be decontaminated;

a flow-through rack assembly supported within the chamber for supporting at least one of the items to be decontaminated, the rack assembly including:
- a fluid flow line which supplies a decontaminant fluid;
- at least one porous hanger for supporting the item, the hanger being formed from a porous material which permits the decontaminant fluid permeate therethrough and contact at least one item, each porous hanger including:
  - a rigid porous member defining a dead end passage therein, the dead end passage being connected with the fluid flow line and the rigid porous member being supported in the chamber.

19. A decontamination system, comprising:

a decontamination chamber;

spray nozzles for spraying a decontaminant fluid on an item in the chamber;

a rack in the chamber on which the item to be decontaminated is suspended, surfaces of the item which contact the rack being shielded from the sprayed decontaminant fluid, the rack including:
- a fluid permeable surface which is directly contacted by a portion of the surface of the suspended item; and a supply of the decontaminant which supplies the decontaminant fluid below the permeable surface under pressure such that the decontaminant fluid flows through the permeable surface wetting the surface portions of the item which contact the rack.

20. The decontamination system of claim 19 further including:

a sump defined in a lowermost portion of the chamber; and, a pump for pumping the decontaminant fluid from the sump and supplying the decontaminant fluid under pressure to the nozzles and the porous hangers.

21. The decontamination system of claim 20, further including:

a decontaminant fluid generating assembly for mixing a strong oxidant with water to form the decontaminant fluid.

22. The decontamination system of claim 20, wherein the flow through rack assembly includes:

a plurality of the porous hangers, each porous hanger extending horizontally to facilitate hanging the items, the porous hangers being deposited at a plurality of elevations.

23. The decontamination system claim 22 wherein:

the fluid flow line includes a rigid system of tubes which provides structural support to a plurality of fittings to which the hangers are connected.

24. A method for microbial decontamination comprising:

supporting an item to be decontaminated on an exterior surface of a side wall of at least one hanger of a flow-through rack assembly, the hanger side wall being fluid permeable to permit a decontaminant fluid to permeate therethrough and contact an exterior surface of the item hanging thereon; and supplying the decontaminant fluid under pressure to the hanger along a fluid flow line, the fluid flowing through an interior passage of the hanger from an open end in fluid communication with the fluid flow line toward a closed end and permeating the fluid permeable hanger side wall and wetting the item exterior surface with the decontaminant fluid.

25. A method of decontamination comprising:

suspending an item to be decontaminated on a rack in a chamber;

spraying a decontaminant liquid on surfaces of the item in the chamber, with surfaces of the item which contact the rack being shielded from the sprayed decontaminant liquid; and supplying a decontaminant liquid through a liquid permeable surface of the rack which is directly contacted by a portion of the surface of the suspended item wetting the surface portions of the item which contact the rack and are shielded from the sprayed liquid.

26. An apparatus for decontaminating comprising:

a plurality of porous hanger means having porous surfaces for hanging an item to be sterilized;

a means for spraying surfaces of the item with a decontaminant fluid, exterior portions of the surfaces of the hangers which are in contact with the item tending to inhibit access to the spray; and a means for passing a portion of the decontaminant fluid under pressure into the porous hanger means and out of porous hanger means only through pores in its porous surfaces, thereby contacting the surface portions of the item in contact with the hangers.

* * * * *